United States Patent
Kent et al.

(10) Patent No.: US 6,307,018 B1
(45) Date of Patent: Oct. 23, 2001

(54) GENERAL CHEMICAL LIGATION

(75) Inventors: Stephen B. H. Kent, San Francisco, CA (US); Tom W. Muir, New York, NY (US); Philip E. Dawson; Steven J. Bark, both of San Diego, CA (US); Lynne Canne Bannen, Pacifica, CA (US)

(73) Assignee: The Scripps Research Institute, La Jollla, CA (US)

( * ) Notice: Subject to any disclaimer, the term of this patent is extended or adjusted under 35 U.S.C. 154(b) by 0 days.

(21) Appl. No.: 09/331,507

(22) PCT Filed: Dec. 24, 1996

(86) PCT No.: PCT/US96/20610

§ 371 Date: Jun. 22, 1999

§ 102(e) Date: Jun. 22, 1999

(87) PCT Pub. No.: WO98/28434

PCT Pub. Date: Jul. 2, 1998

(51) Int. Cl.[7] .......................................................... C07K 1/00
(52) U.S. Cl. .......................... 530/333; 530/338; 530/339; 530/345
(58) Field of Search .................................... 530/333, 338, 530/339, 345

(56) References Cited

U.S. PATENT DOCUMENTS 5,589,356 * 12/1996 Tam ...................................... 435/68.1
5,625,030    4/1997 Williams et al. ..................... 528/361

FOREIGN PATENT DOCUMENTS

96/34878 * 11/1996 (WO) .
98/28434 *  7/1998 (WO) .

OTHER PUBLICATIONS

Gennari, Tetrahedron 46, 7289, 1990.*
Muir, Methods Enzymol. 289, 266–298, 1997.*
Dawson, J. Am. Chem. Soc. 119, 4325, 1997.*
Canne, J. Am. Chem. Soc. 121, 8720, 1999.*
Wilken, Curr. Opin. Biotechnol 9, 412–426, 1998.*
Liu, Proc. Natl. Acad. Sci. 91, 6584–88, 1994.*
Dawson, Science 266, 776–779, 1994.*
Wieland, et al., "Über Peptidsynthesen. 8. Mitteilung Bildung von S–haltigen Peptiden durch intramolekulare Wanderung von Aminoacylresten", Liebigs. Ann. Chem. 583: 129–149 (1953).
Fotouhi, et al., "Peptide Synthesis by Prior Thiol Capture. 6. Rates of the Disulfide Bond Forming Capture Reaction and Demonstration of the Overall Strategy by Synthesis of the C–Terminal 29–Peptide Sequence of BPTI", J. Org. Chem. 54: 2803–2817 (1989).

Schnölzer, et al., "Constructing Proteins by Dovetailing Unprotected Synthetic Peptides: Backbone–Engineered HIV Protease", Science 256: 221–225 (1992).

Schnölzer, et al., "In situ Neutralization in Boc–Chemistry Solid Phase Peptide Synthesis", Int. J. Pept. Prot. Res. 40: 180–193 (1992).

Dawson, et al., "Convenient Total Synthesis of a 4–Helix TASP Molecule by Chemoselective Ligation", J. Am. Chem. Soc. 115: 7263–7266 (1993).

Rose, "Facile Synthesis of Homogeneous Artificial Proteins", J. Am. Chem. Soc. 116: 30–33 (1994).

Liu, et al., "Peptide Segment Ligation Strategy Without use of Protecting Groups", Proc. Natl. Acad. Sci. USA 91: 6584–6588 (1994).

Muir, et al., "Design and Chemical Synthesis of a Neoprotein Structural Model for the Cytoplasmic Domain of a Multisubunit Cell–Surface Receptor: Integrin $\alpha_{IIb}\beta_3$ )Platelet GPIIb–IIIa)", Biochem. 33: 7701–7708 (1994).

Dawson, et al., "Synthesis of Proteins by Native Chemical Ligation", Science 266: 776–779 (1994).

Williams, et al., "Total Chemical Synthesis of a Folded β–Sandwich Protein Domain: An Analog of the Tenth Fibronectin Type 3 Module", J. Am. Chem. Soc. 116: 10797–10798 (1994).

Baca, et al., "Chemical Ligation of Cysteine–Containing Peptides: Synthesis of a 22 kDa Tethered Dimer of HIV–1 Protease", J. AM. Chem. Soc. 117: 1881–1887 (1995).

Canne, et al., "Total Chemical Synthesis of a Unique Transcription Factor–Related Protein: cMyc–Max", J. Am. Chem. Soc. 117: 2998–3007 (1995).

Liu, et al., "Acyl Disulfide–Mediated Intramolecular Acylation for Orthogonal Coupling Between Unprotected Peptide Segments. Mechanism and Application.", Tet. Lett. 37: 933–936 (1996).

* cited by examiner

Primary Examiner—Christopher S. F. Low
Assistant Examiner—David Lukton
(74) Attorney, Agent, or Firm—Donald G. Lewis (57) ABSTRACT

Disclosed herein is a process whereby oligopeptides are ligated to form ligation peptide products. In the first step, two starting oligopeptides are ligated to form an intermediate having an amino-thioester linkage. In the second step, the aminothioester linkage undergoes a rearrangement to form a peptide having an N-substituted amide linkage. In an optional third step, the N-substitution of the amide linkage is chemically removed to form a native peptide linkage.

8 Claims, 6 Drawing Sheets

| Example Ligation | Peptide 1[a] | Peptide 2[b] | pH | Temp. (°C) | Reaction time (hrs) | Unrearranged product (3) | Rearranged product (4) |
|---|---|---|---|---|---|---|---|
| 1 | LYRAG-SNB | Nα(etsh)-GAGPAGD | 7.0 | 25 | 4 | not detected | 90% |
| 2 | LYRAG-SNB | Nα(oetsh)-GRNTATIMMQRGNFR | 7.5 | 25 | 16 | not detected | 75% |
| 3 | LYRAG-Sbzl | Nα(oetsh)-GRNTATIMMQRGNFR | [7.5<br>4.5[d] | 37<br>37 | 11.5<br>10 | 30%<br>0% | (35%)]<br>64% |
| 4 | LYRAE-Sbzl | Nα(oetsh)-AARHTVHQRHLHG | [7.5<br>4.5[d] | 37<br>37 | 17.5<br>6.5 | 39%<br>20% | (52%)]<br>69% |
| 5 | LYRAE-Sbzl | Nα(oetsh)-AARHTVHQRHLHG | 7.5<br>4.5[d] | 37<br>37 | 19<br>22 | 58%<br>52% | not detected<br>not detected |

GENERAL CHEMICAL LIGATION

This application is a 371 of PCT/US96/20610, filed Dec. 24, 1996.

GOVERNMENT RIGHTS

This invention was made with government support under Contract Nos. GM 48897 and GM 48870 by the National Institutes of Health. The government has certain rights in the invention.

TECHNICAL FIELD OF THE INVENTION

The present invention relates to methods for chemically ligating oligopeptides. More particularly, the invention relates to methods for chemically ligating oligopeptides end to end using a peptide bond.

BACKGROUND OF THE INVENTION

The synthesis of peptides by conventional stepwise solid phase methodologies is limited by low yields when synthesizing long peptides. (Merrifield et al. *J. Am. Chem. Soc.* 1963, 85, 2149–2154; Kent et al. *Ann. Rev. Biochem.* 1988, 57, 957–989.) To overcome this limitation, smaller synthetic peptides may be joined to one another by chemical ligation to produce longer peptide products.

A method for chemically ligating peptides was disclosed by Schnölzer et al.. (Schnölzer et al., *Science* 1992, 256, 221–225; Rose et al. *J. Am. Chem. Soc.* 1994, 116, 30–34; Liu et al. *Proc. Natl. Acad. Sci. USA* 1994, 91, 6584–6588). The methodology disclosed by Schnölzer involves a chemoselective reaction of unprotected peptide segments to give a product with an unnatural backbone structure at the site of ligation. This methodology makes possible the synthesis of peptides of greater size than attainable by standard methods of peptide synthesis. (Canne et al. *J. Am. Chem. Soc.* 1995, 117, 2998–3007; Baca et al. *J. Am. Chem. Soc.* 1995, 117, 1881–1887; Williams et al. *J. Am. Chem. Soc.* 1994, 116, 10797–10798). This methedology also makes possible the synthesis of peptides of unusual structure and topology. (Dawson et al. *J. Am. Chem. Soc.* 1993, 115, 7263–7266; Rose et al. *J. Am. Chem. Soc.* 1994, 116, 30–34; Muir et al. *Biochemistry* 1994, 33, 7701–7708; Canne et al. *J. Am. Chem. Soc.* 1995, 117, 2998–3007). The combined use of conventional stepwise solid phase peptide synthesis together with chemical ligation enables chemists to routinely make unprotected peptides of up to 60 amino acid residues in good yield and purity. (Schnölzer et al. *Int. J. Pept. Protein Res.* 1992, 40, 180–193). The combination of these two methodologies may also be employed to achieve a total chemical synthesis of proteins.

Another chemical ligation technique has been reported for the preparation of proteins having a native backbone structure (Dawson et al. *Science* 1994, 266, 776–779). This mode of chemical ligation is termed "native ligation." In this technique, an unprotected synthetic peptide bearing a C-terminal α-thioester is reacted in a chemoselective manner with an unprotected peptide containing an N-terminal Cys residue. Thiol exchange reaction yields an intial thioester-linked intermediate which spontaneously rearranges to give a native amide bond at the ligation site joining the two peptide segments, in the process regenerating the Cys side chain thiol. This version of native ligation uses chemistry first described by Wieland for reacting amino acids. (Wieland et al. *Liebigs Ann. Chem.* 1953, 583, 129–149.) As originally described, native ligation is restricted to joining peptide segments at an X-Cys bond. (Dawson et al. *Science* 1994, 266, 776–779.)

What is needed is a general method for joining a C-terminal α-thioester peptide segment to an N-terminal amino acid peptide segment, wherein the N-terminal amino acid peptide segment need not have an N-terminal cysteine.

SUMMARY OF THE INVENTION

The invention is directed to a method for chemically ligating unprotected oligopeptides to form a product having all peptide linkages. In the first step, two oligopeptides are ligated to form a ligation product having an aminothioester linkage. In the second step, the aminothioester linkage rearranges to form a product having an N-substituted amide linkage. In an optional third step, the substitution on the amide bond is removed by facile treatment with Zn in acidic medium, to give a native peptide bond at the ligation site.

The method employs two starting oligopeptides, viz., a first starting oligopeptide and a second starting oligopeptide. The first oligopeptide has a C-terminal auxiliary group with a thioester moiety, i.e., $[\text{peptide}_1]^\alpha\text{COSR}$, where R is selected from the group consisting of 3-carboxy 4-nitrophenyl and benzyl. The second oligopeptide has an N-terminal auxiliary functional group with an unoxidized sulfhydryl moiety, i.e., $\text{HSCH}_2\text{CH}_2(\text{O})\text{-N}^\alpha[\text{peptide}_2]$. When the first and second starting oligopeptides are admixed under conditions promoting thioester exchange, they condense with one another to form an intermediate oligopeptide product wherein the first and second oligopeptides are linked via an amino-thioester bond. The amino-thioester bond then spontaneously rearranges intramolecularly to form a ligation product linked by an N-substituted amide bond. During the intramolecular rearrangement, the amino group of the N-terminal auxiliary functional group atacks the thioester to form an amide bond with the attached N-linked auxiliary functional group containing a displaced sulfhydryl moiety. The N-linked auxiliary functional group containing the displaced sulfhydryl moiety may then be optionally removed by chemical means to form a product having all native peptide linkages.

One aspect of the invention is directed to a method for ligating a first oligopeptide with a second oligopeptide end to end for producing an oligopeptide product. More particularly, the method comprises two steps with an optional third step.

The first step involves condensing the C-terminal thioester of a first peptide with the unoxidized sulfhydryl moiety of a second oligopeptide for producing an intermediate oligopeptide linking the first and second oligopeptides with an δ or γ-amino-thioester bond. The first oligopeptide includes the C-terminal thioester on a C-terminal residue and the second oligopeptide includes the N-terminal auxiliary functional group on an N-terminal residue having an unoxidized sulfhydryl moiety. If the C-terminal residue on the first oligopeptide is non glycine then the N-terminal residue on the second oligopeptide is glycine and if the N-terminal residue on the second oligopeptide is non glycine then the C-terminal residue on the first oligopeptide is glycine with the proviso that the non glycine residue is a non β-branched amino acid.

The second step rearranges the δ or γ-amino-thioester bond of the intermediate oligopeptide via intramolecular attack of the δ or γ-amino group onto the thioester moiety and displaces a sulfhydryl moiety as a byproduct from the thioester moiety thereby producing an oligopeptide product linking the first and second oligopeptides with an amide bond. The nitrogen of the amide bond contains the auxiliary functional group with the displaced sulfhydryl moiety.

An optional third step involves the removal of the auxiliary functional group on the amide nitrogen, from the oligopeptide product with a reducing agent for producing a native peptide bond. The amide nitrogen auxiliary functional group is N̲-α-O—$(CH_2)_n$—SH wherein $1 \leq n \leq 2$ and the reducing agent is Zinc (underlined nitrogen represents the coupled amide nitrogen).

Another aspect of the invention includes the oligopeptide intermediate comprising a first oligopeptide segment including a C-terminal thioester, a second oligopeptide segment including an N-terminal auxiliary functional group having an unoxidized sulfhydryl moiety, and an aminothioester linkage unit linking the C-terminal thioester and the sulfhydryl group of the auxiliary functional group.

DESCRIPTION OF FIGURES

FIG. 4 shows a table with summaries of model ligations for Examples #1–5. Superscript is as follows: (a) Thioester peptides where -SNB=3-carboxy-4-nitrophenyl thioester and -Sbzl=benzyl thioester; (b) $N^\alpha$(substituted) peptides where etsh=$N^\alpha$(ethanethiol)- and oetsh=$N^\alpha$(oxyethanethiol)-; (c) Based on Peptide 2, estimated from analytical reverse phase HPLC (peak areas) and ESMS; (d) Adjusted to pH 4.5 after the indicated hrs at pH 7.5. The unique peptides under the heading 1a can be found respectively in SEQ ID NOs 1, 19, and 6. The unique peptides under the heading 2a can be found respectively in SEQ ID NOs 23–25.

FIGS. 5A–5C illustrate the model ligation, Example #2 (infra), to form amide -Gly($N^\alpha$—$OCH_2CH_2SH$)Gly- compound 4b carried out in 6 M guanidine.HCl, 0.1 M $Na_2HPO_4$, pH 7.5. (A)–(C) represent HPLC plots as follows: (A) Analytical HPLC (10–50%B over 30 min) at t=0; peak a, thioester peptide, 1, LYRA G̲-$^\alpha COSC_6H_3(3-CO_2H-4-NO_2)$ (SEQ ID NO 1); peak b, $N^\alpha$(oxyethanethiol) peptide, 2b, [$HSCH_2CH_2O$]-GRNTATIMMQRGNFR-$^\alpha CONH_2$(SEQ ID NO 4); (B) Analytical HPLC (10–50%B over 30 min) at t=1 h; peak c, non-peptide impurity; peak d, LYRAG-$^\alpha COSC_6H_5$, resulting from transthioesterification of 1 (peak a) with thiophenol; peak e, intermediate ligation product, 4b, LYRA GG̲($N^\alpha$-$OCH_2CH_2SH$)RNTATIMMQRGNFR-$^\alpha CONH_2$(SEQ ID NO 5); and a minor amount of unreacted [$HSCH_2CH_2O$]-GRNTATIMMQRGNFR (SEQ ID NO 4)-$^\alpha CONH_2$ (2b), as determined by electrospray ionization MS. (C) Analytical HPLC (15–40%B over 30 min) of peak e after HPLC-purification and treatment with Zn in acidic HPLC solvent overnight; peak, f, final ligation product, 5b, LYRA GGRNTATIMMQRGNFR-$^\alpha CONH_2$(SEQ ID NO 15); peak g, non-peptide impurity.

FIGS. 6A–6C illustrate the model ligation, Example #3 (infra) to form a -Phe($N^\alpha$—$OCH_2CH_2SH$)Gly- linked product 4b. Ligation and rearrangement carried out at 37° C. (A)–(C) represent HPLC plots as follows: (A) Analytical HPLC (20–40%B over 30 min) after 11.5 h in 6 M guanidine.HCl, 0.1 M $Na_2HPO_4$, pH 7.5; peak a, $N^\alpha$(oxyethanethiol) peptide, 2b, [$HSCH_2CH_2O$]-GRNTATIMMQRGNFR-$^\alpha CONH_2$(SEQ ID NO 4); peak b, unrearranged intermediate ligation product, 3b, LYRA F̲-[$^\alpha COSCH_2CH_2O$]-GRNTATIMMQRGNFR-$^\alpha CONH_2$(SEQ ID NO 8); peak c, rearranged intermediate ligation product, 4b, LYRA FG̲($N^\alpha$-$OCH_2CH_2SH$)RNTATIMMQRGNFR-$^\alpha CONH_2$; peak d, thioester peptide, 1, LYRAF̲-$^\alpha COSCH_2C_6H_5$(SEQ ID NO 9). (B) Analytical HPLC (20–40%B over 30 min) after 10 h in 6 M guanidine.HCl, 0.1 M $NaCH_3CO_2$, pH 4.5. (C) Analytical HPLC (0–67%B over 30 min) of HPLC-purified peak c after treatment with Zn in acidic HPLC solvent overnight; peak f, final ligation product, 5b, LYRA F̲GRNTATIMMQRGNFR-$^\alpha CONH_2$(SEQ ID NO 18).

DETAILED DESCRIPTION OF THE INVENTION

The invention is directed to a two step method for chemically ligating together two seperate peptide fragments. More particularly, the invention relates to a general methodology for native (amide-forming) chemical ligation of unprotected peptide segments to produce a native peptide bond.

Step 1 comprises the condensation of a C-terminal thioester of a first peptide with an unoxidized sulfhydryl moiety of a second oligopeptide and produces an intermediate oligopeptide which links the first and second oligopeptides with an δ or γ-amino-thioester bond. If the C-terminal residue on the first oligopeptide is non glycine then the N-terminal residue on the second oligopeptide is glycine and if the N-terminal residue on the second oligopeptide is non glycine then the C-terminal residue on the first oligopeptide is glycine with the proviso that the non glycine residue is a non β-branched amino acid.

Step 2 comprises the rearrangement of the δ or γ-aminothioester bond of the intermediate oligopeptide via intramolecular attack of the δ or γ-amino group onto the thioester moiety which displaces a sulfhydryl moiety as a byproduct from the thioester moiety and produces an oligopeptide product linking the first and second oligopeptides with a native amide bond. The nitrogen of the amide bond, however, contains the auxiliary functional group with the displaced sulfhydryl moiety.

An optional third step comprises the removal of the auxiliary functional group on the amide nitrogen, from the oligopeptide product with a reducing agent and produces a native peptide bond. The amide nitrogen auxiliary functional group is, N̲-α-O—$(CH_2)_n$—SH wherein $1 \leq n \leq 2$ and the reducing agent is Zinc (underlined nitrogen represents the coupled amide nitrogen).

Figure 1:
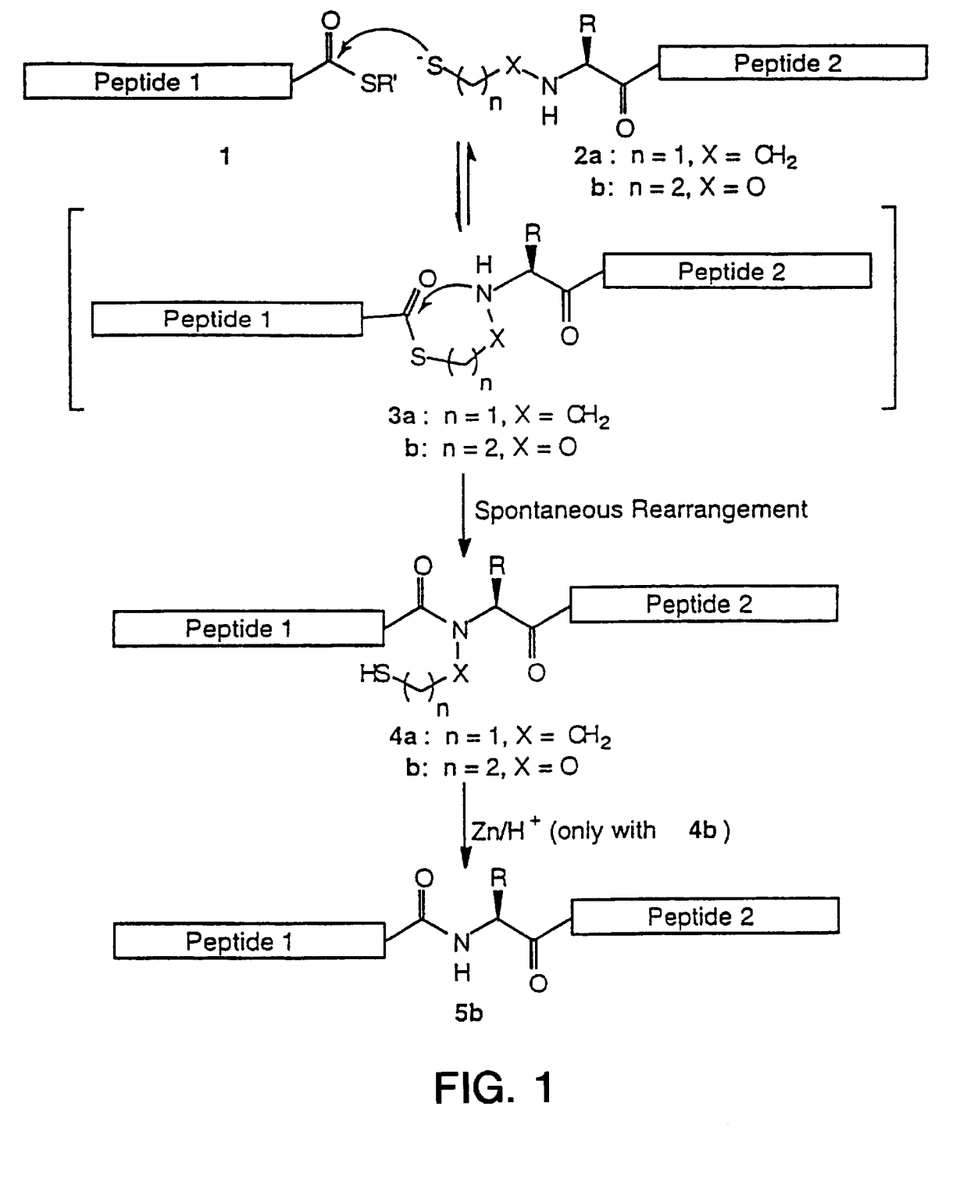
FIG. 1 illustrates the generalized native chemical ligation of unprotected peptide segments wherein R is a non β-branched amino acid residue with the following conditions: if the C-terminal residue on the first oligopeptide is non glycine then the N-terminal residue on the second oligopeptide is glycine and if the N-terminal residue on the second oligopeptide is non glycine then the C-terminal residue on the first oligopeptide is glycine. R' is selected from the group consisting of 3-carboxy 4-nitrophenyl and benzyl.

The method allows for the synthesis of peptides and proteins with either native or modified backbone structures. FIG. 1 outlines the procedure. The peptide α-carboxythioester (1) reacts, via thiol exchange, with either an $N^\alpha$(ethanethiol) peptide (2a) or an $N^\alpha$(oxyethanethiol) peptide (2b) to produce the ligation product 3. This thioester-linked intermediate rearranges through a favorable geometric arrangement involving a 5- or 6-membered ring to give the amide-linked product 4, containing a secondary amide in 4a or the analogous N-oxyalkyl compound in 4b. The resulting $N^\alpha$(substituted)amides also have potentially favorable solubility properties (Quibell et al. *J. Am. Chem.*

Soc. 1995, 117, 11656–11668) the N-$^\alpha$(O-alkyl)amide ligation product has the further advantage of being stable to HF cleavage conditions, yet is simply removed under mild conditions. In the case of 4b, zinc dust can be added directly to the reverse phase HPLC-purified peptide in the acidic eluant to reduce the N—O bond of the O-alkoxyhydroxamate and give the native backbone structure of ligation product 5b.

All peptide segments were synthesized in stepwise fashion by established solid phase methods using in situ neutralization/2-(1H-benzotriazol-1-yl)-1,1,3,3-tetramethyluronium hexafluorophosphate (HBTU) activation protocols for tert-butoxycarbonyl (Boc) chemistry, purified by preparative reverse phase HPLC, and characterized by electrospray mass spectrometry (ESMS) (Schnölzer et al. Int. J. Pept. Protein Res. 1992, 40, 180–193). Peptide-$\alpha$-thioesters (1) were generated from the corresponding peptide-$\alpha$-thioacids, which in turn, were synthesized on a thioester resin as described in Canne et al. Tetrahedron Lett. 1995, 36, 1217–1220). The peptide-$\alpha$-thioacids were converted to either the corresponding 3-carboxy-4-nitrophenyl thioesters in 6 M guanidine.HCl, 0.1 M Na acetate, pH 5.0–6.5, by reaction with 1.5 equivalents of 5,5'-dithio-bis (2-nitrobenzoic acid) or to the corresponding benzyl ester in 6M guanidine.HCl, 0.1 M Na acetate, pH 4.0, using 10 equivalents of benzyl bromide (Dawson et al. Science 1994, 266, 776–779). Both these thioesters provide satisfactory leaving groups for the ligation reactions, with the 3-carboxy-4-nitrophenyl thioesters demonstrating a somewhat faster reaction rate than the corresponding benzyl thioesters (Dawson et al. Science 1994, 266, 776–779).

Figure 2:
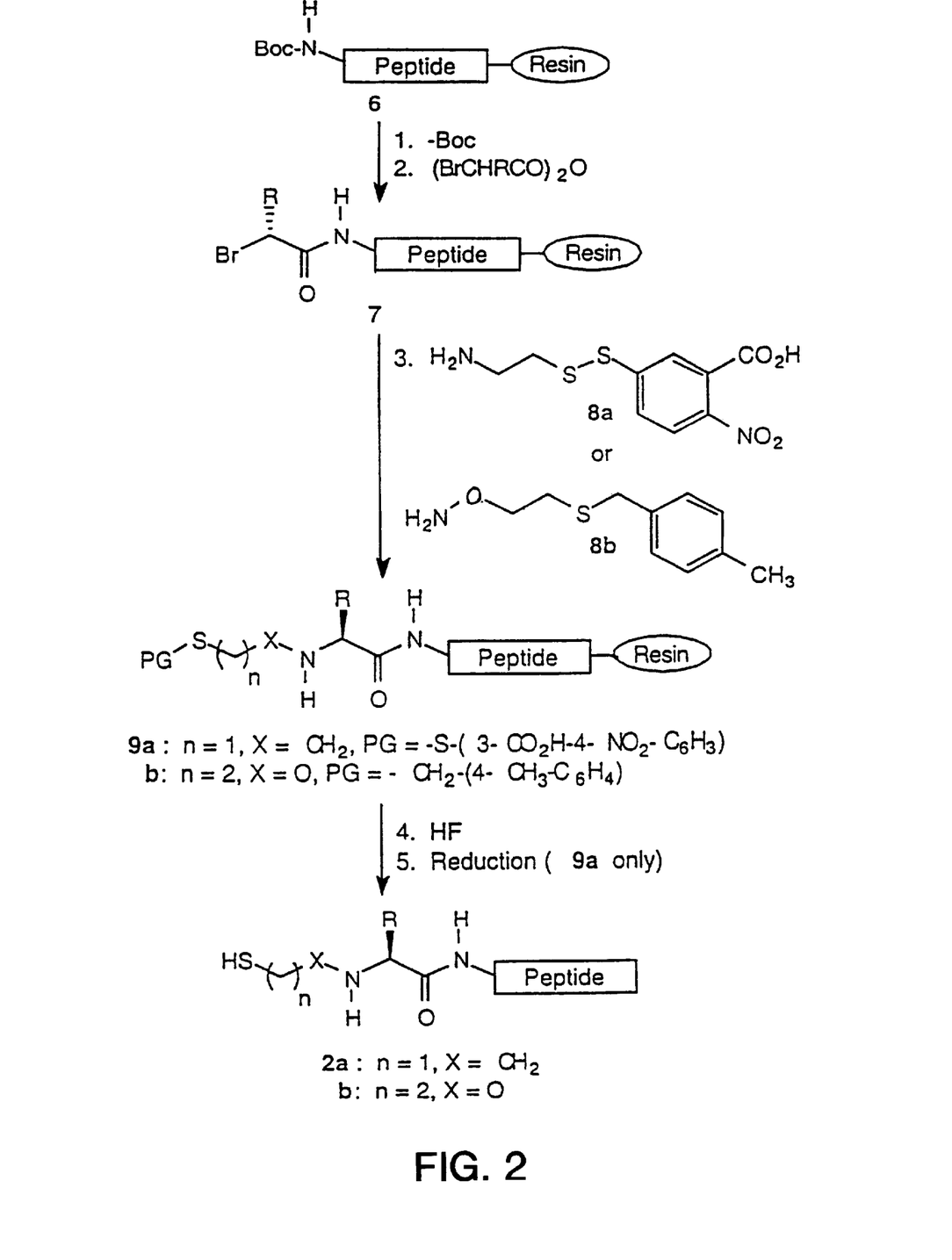
FIG. 2 illustrates the chemical synthesis of $N^\alpha$(substituted) peptide segments 2a and 2b.

The syntheses of N$^\alpha$(ethanethiol)- (2a) and N$^\alpha$(oxyethanethiol)- peptides (2b) are illustrated in FIG. 2. The appropriate $\alpha$-bromocarboxylic acid, activated as the symmetric anhydride (0.5 equivalents 1,3-diisopropylcarbodiimde (DIC) in dichloromethane) (Robey et al. Anal. Biochem. 1989, 177, 373–377) was coupled to the deprotected N-terminal amino acid of peptide-resin 6 to give bromoacyl-peptide-resin 7. The bromide was then displaced, with inversion of stereochemistry, by the amine function of either structure 8a or 8b in DMSO to give peptide-resin 9. Deprotection and cleavage from the resin in anhydrous HF gave 2b directly or 2a still in the form of the disulfide which was reduced to the free thiol.

Figure 3:
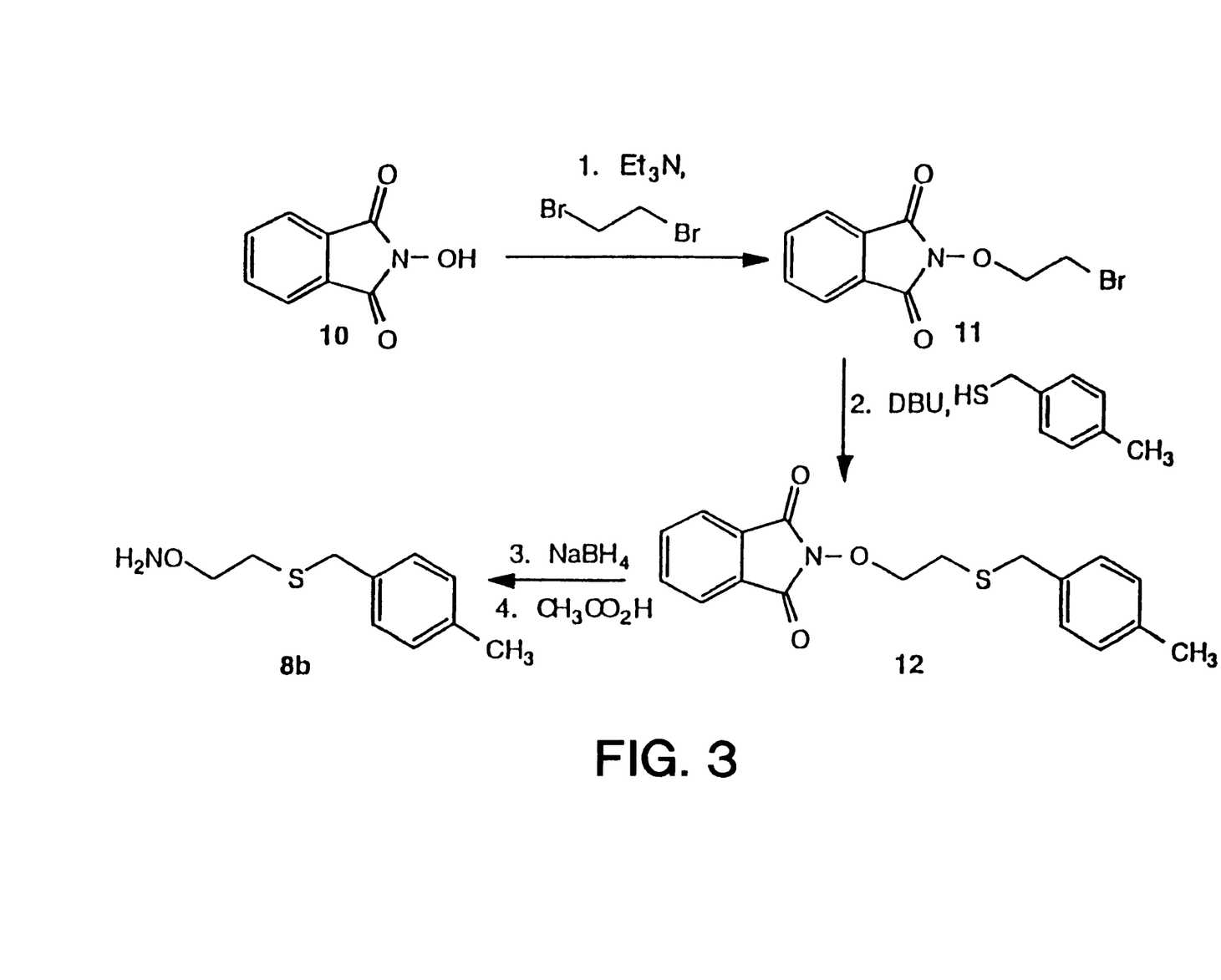
FIG. 3 illustrates the chemical synthesis of compound 8b.

The aminoethanethiol derivative 8a was synthesized in one step from the reaction of 2-aminoethanethiol and 5,5'-dithio-bis(2-nitrobenzoic acid) in 80% acetonitrile in water. The synthesis of the aminooxyethanethiol derivative 8b was more involved and is illustrated in FIG. 3. Bromide 11 was produced from the reaction of N-hydroxyphthalimide (10) with a large excess of 1,2-dibromoethane (Bauer J. Org. Chem. 1963, 28, 1604–1608). Bromide 11 was then converted to the protected aminooxyethanethiol derivative 12 with 4-methylbenzyl mercaptan in the presence of the base 1,8-Diazabicylco[5.4.0]undeC-7-ene (DBU). The phthalimide group of 12 was removed in a two step process (Osby et al. Tetrahedron Lett. 1984, 25, 2093–2096) involving reduction with NaBH$_4$ followed by treatment with acetic acid to give the desired aminooxyethanethiol derivative 8b.

Compared with the original native chemical ligation at X-Cys sites (Dawson et al. Science 1994, 266, 776–779), the most notable feature of the ligation chemistry of this invention is the slower rearrangement of the initial thioester ligation product. Intramolecular attack by the $\alpha$-NH(O-alkyl) group via a six-membered ring intermediate in the current instance is considerably less favored (Mandolini et al. J. Am. Chem. Soc. 1978, 100, 550–554) than the facile five-membered ring mediated attack of the unsubstituted $\alpha$-NH$_2$ group in the X-Cys ligation (Dawson et al. Science 1994, 266, 77614 779). Except for the Gly-Gly ligation, one is able to isolate the thioester-linked initial ligation product of the present invention (FIG. 4), which rearranged only slowly. Remarkably, for C$^\alpha$-substituted amino acids on both sides of the ligation site, one is unable to observe susbsequent rearrangement to an amide bond: the thioester-linked intermediate was indefinitely stable under the conditions of reaction. These slow rearrangements are similar to those observed in an (N-substituted)amide-forming ligation chemistry previously described (Liu et al. Proc. Natl. Acad. Sci. USA 1994, 91, 6584–6588).

The use, in the invention, of a temporary auxiliary functional group in amide-forming ligation is reminiscent of the 'thiol capture' strategy proposed by Kemp (Fotouhi et al. J. Org. Chem. 1989, 54, 2806–2817). Both native chemical ligation and the thiol-capture method have as their stated goal the use of unprotected peptides in a segment condensation strategy to achieve the synthesis of long polypeptide chains. The key aspect of the native chemical ligation approach is reaction under conditions that promote exchange of the thiol moiety of the initial thioester-linked intermediate products, to give regioselective ligation at the N-terminal Cys even in the presence of other Cys residues in both segments (Dawson et al. Science 1994, 266, 776–779). By contrast, in the 'thiol capture' strategy and related methods (Liu et al. Tetrahedron Lett. 1996, 37, 933–936) regiospecific protection of Cys side chain functionalities prior to the ligation reaction is a necessity (Kemp et al. Peptides: Proceedings of the 11th American Peptide Symposium Rivier, J. E.; Marshall, G. R., Eds, ESCOM: Lieden, 1990; pp 920–922), thus frustrating their original intent.

Similarly, the use, in the current invention, of a carbonyl-activated $\alpha$-thiocarboxyl function (i.e. an $\alpha$-COSR) is reminiscent of chemistry previously used in peptide segment condensation (Blake et al. Proc. Natl. Acad. Sci. USA 1981, 78, 4055–4058; Yamashiro et al. Int. J. Pept. Protein Res. 1988, 31, 322–334; Hojo et al. Peptide Chemistry Okada, Y., Ed, Protein Research Foundation: Osaka, 1994; pp 9–12) However, these syntheses were based on conventional noN-chemoselective attack by the $\alpha$-amine nucleophile of the second segment on a Ag$^+$-activated peptide-$^\alpha$COSR, and thus necessitated regiospecific (re)protection of all other $\alpha$- and $\epsilon$-amine functional groups in both segments.

By contrast, thioester-mediated amide-forming ligation chemistry is compatible with the use of completely unprotected peptide segments with the full range of side chain functionalities found in nature, including thiols (Baca et al. J. Am. Chem. Soc. 1995, 117, 1881–1887; Dawson et al. Science 1994, 266, 776–779). For this reason, native chemical ligation is simple, practical, and is a general approach to the total chemical synthesis of proteins provided they contain appropriate ligation sites.

This invention increases the utility of the native chemical ligation method reported by Dawson, et al (Dawson et al. Science 1994, 266, 776–779) by extending the number of dipeptide sequences that can be used as ligation sites. In addition to the X-Cys ligation site of that methodology, it is disclosed herein how make use of X-Gly and Gly-X ligation sites (i.e. the C-terminal residue being glycine if the N-terminal residue is non-glycine or conversely, the N-terminal residue being glycine if the C-terminal residue is non-glycine). In the preferred mode, X is any of the non-$\beta$-branched amino acids. However, our previous studies have shown that X can be any amino acid, including $\beta$-branched such as Val;(Dawson et al. Science 1994, 266, 776–779).

The invention potentially extends the number of suitable sites for native chemical ligation by a factor of three, to more than 50 of the 400 dipeptide sequences found in proteins. Because there is considerable latitude in choosing a ligation site in a target sequence which contains a glycine residue, this extended applicability will render most polypeptides accessible by native chemical ligation.

Native chemical ligation in its original form (Dawson et al. *Science* 1994, 266, 776–779) or in the form described here provides direct synthetic access to polypeptide chains the size of typical protein domains. Other ligation chemistries (Schnölzer et al. *Science* 1992, 256, 221–225; Rose et al. *Am. Chem. Soc.* 1994, 116, 30–34; Liu et al. *Proc. Natl. Acad. Sci. USA* 1994, 91, 6584–6588) can be used to join synthetic domains in a modular fashion to produce large (i.e. >20 kilodalton), fully functional synthetic proteins (Canne et al. *J. Am. Chem. Soc.* 1995, 117, 2998–3007; Baca et al. *J. Am. Chem. Soc.* 1995, 117, 1881–1887). In its most general form, incorporating all suitable chemistries (Dawson et al. *Science* 1994, 266, 776–779) the chemical ligation approach represents the next stage in the evolution of methods for the chemical synthesis of polypeptides and, for the first time, provides for reproducible, practical total chemical synthesis of proteins.

Example Ligations 1–4

Figure 4:
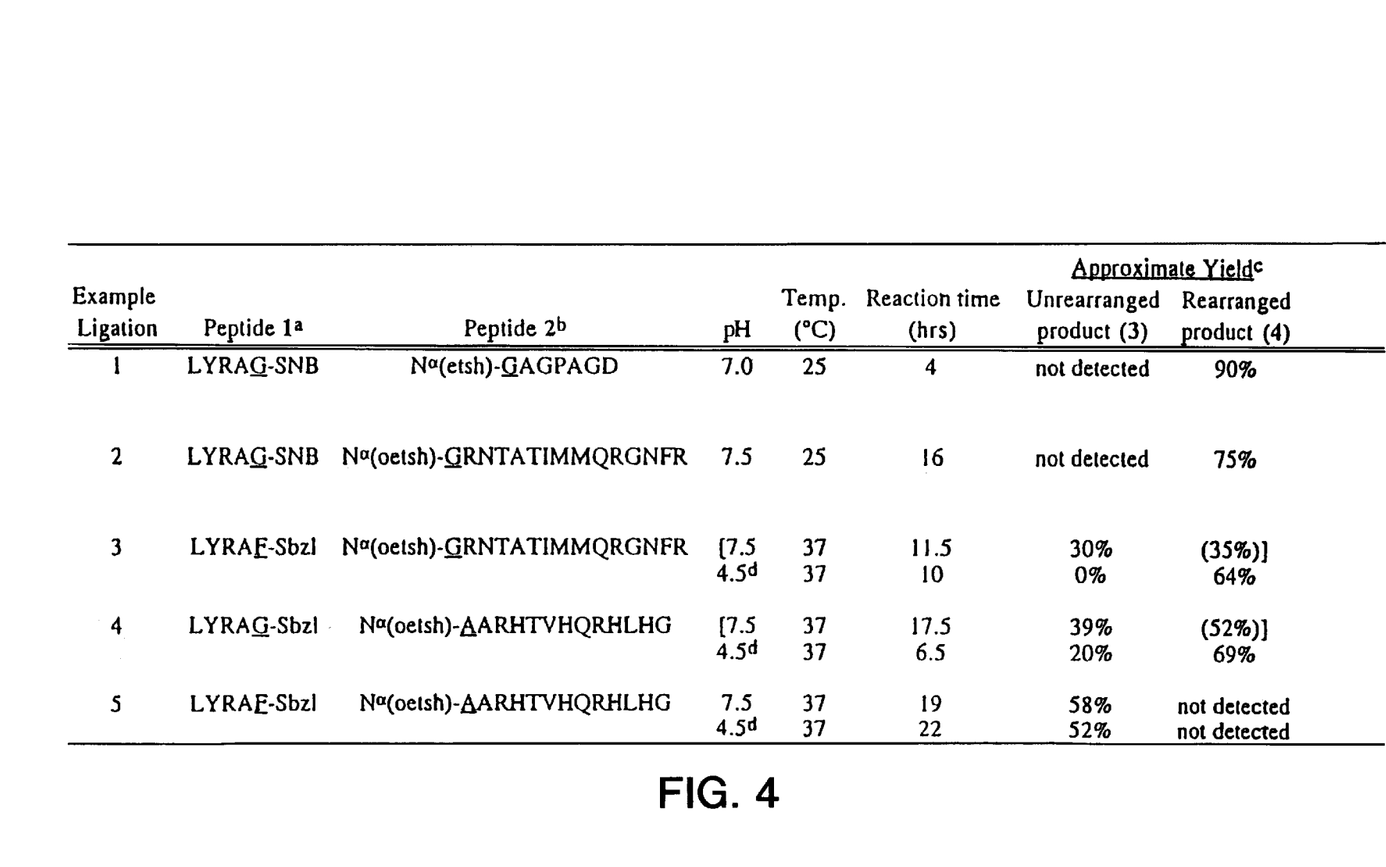

Results of example ligations are summarized in FIG. 4. All ligations were run at concentrations ranging from 4 mgs/mL to 8 mgs/mL of each peptide in either 8M Urea, 0.1 M $Na_2HPO_4$, pH 7.0 or 6M guanidine.HCl, 0.1 M $Na_2HPO_4$, pH 7.5. Immediately after solvation of the peptide segments, 2–5% benzyl mercaptan (example ligation #1) or thiophenol (example ligations #2–5), by volume of ligation buffer, was added to keep thiol functions in the reduced form. This had the added consequence of exchanging a significant amount of the original peptide-$^\alpha$thioester (1) to a peptide-$^\alpha$thiobenzyl ester or peptide-$^\alpha$thiophenyl ester, both of which are still capable of reacting in the desired fashion with peptide 2. The ligation reactions were followed by analytical reverse-phase HPLC and the products identified by ESMS. In the following examples, the amino acid residues involved in the ligation are underlined.

EXAMPLE 1

The peptide-$^\alpha$thio(3-carboxy-4-nitro)phenyl ester 1 had the sequence LYRA<u>G</u>-$^\alpha$COSC$_6$H$_3$(3-CO$_2$H-4-NO$_2$) (SEQ ID NO 1) (observed mass 760 Da, calcd 760 Da). The N$^\alpha$(ethanethiol) peptide 2a, protected as the 5-thio-2-(nitrobenzoic acid) disulfide, had the sequence [(3-CO$_2$H-4-NO$_2$)—C$_6$H$_3$—S—SCH$_2$CH$_2$]-<u>G</u>AGPAGD-$^\alpha$CONH$_2$ (SEQ ID NO 2) (observed mass 800 Da, calcd 800 Da) which was reduced to [HSCH$_2$CH$_2$]-<u>G</u>AGPAGD-$^\alpha$CONH$_2$ (SEQ ID NO 13) (observed mass 603 Da, calcd 603 Da) in the ligation mixture. After one hour, the product of the ligation, 4a, [LYRA<u>GG</u>(N$^\alpha$—CH$_2$CH$_2$SH)AGPAGD-$^\alpha$CONH$_2$ (SEQ ID NO 3) (observed mass 1163±1 Da, calcd 1163 Da)] had already formed to a significant degree. After purification of the ligation product by reverse phase HPLC, it was treated with 5,5'-dithio-bis(2-nitrobenzoic acid) for one hour in 6 M urea, 0.1 M phosphate, pH 6.0 to yield the expected —S-nitrobenzoic acid disulfide product, LYRA<u>GG</u>[N$^\alpha$—CH$_2$CH$_2$S—SC$_6$H$_3$(3-CO$_2$H-4-NO$_2$)]AGPAGD-$^\alpha$CONH$_2$ (SEQ ID NO 7) (observed mass 1360±1 Da, calcd 1360 Da). This confirmed the rearrangement of 3a to form 4a, since 3a would have been unreactive towards 5,5'-dithio-bis(2-nitrobenzoic acid). The results are summarized in FIG. 4.

EXAMPLE 2

Figure 5A:
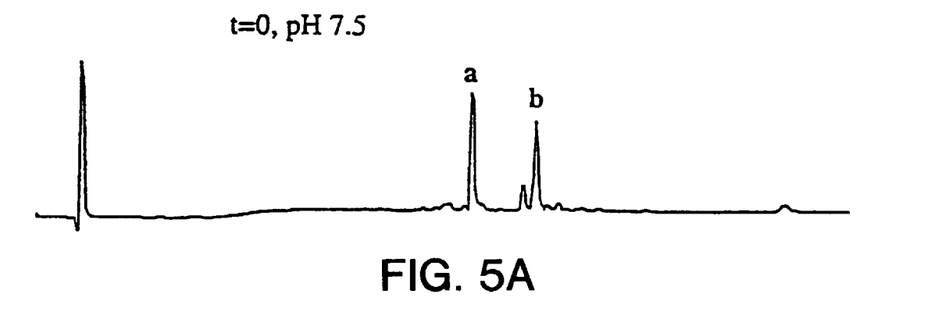
Figure 5B:
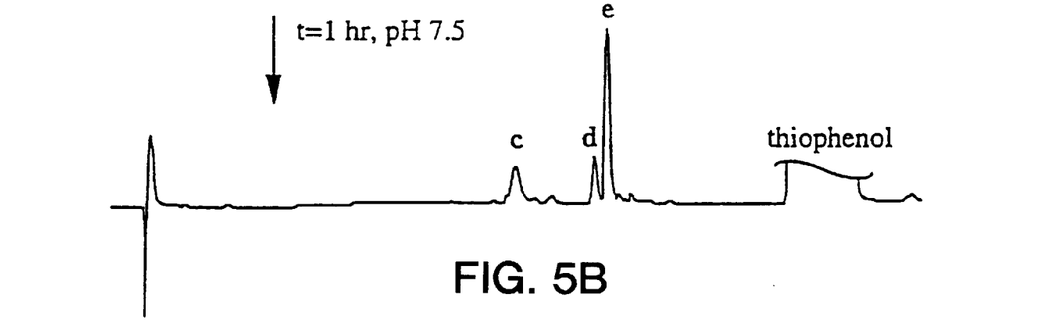
Figure 5C:
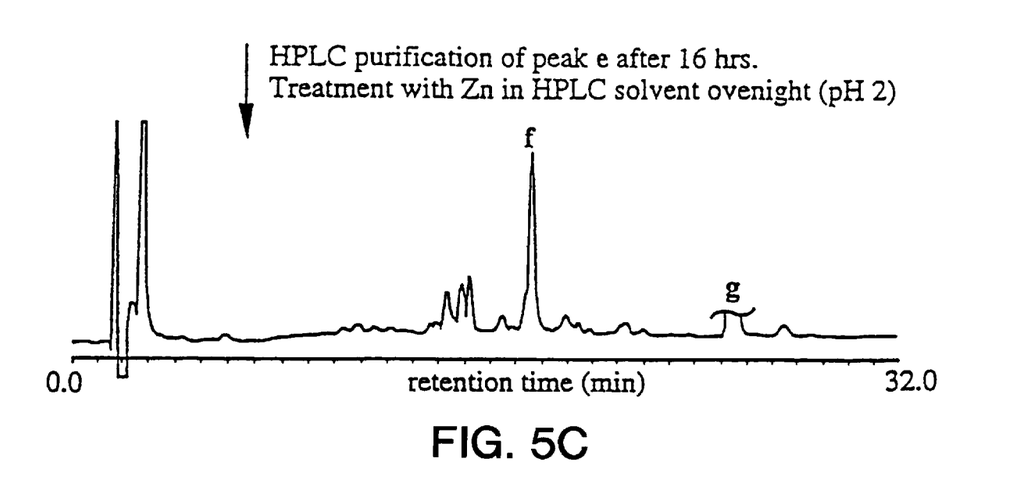

FIGS. 5A–5C show the course of example ligation #2. The peptide thioester segment 1 (peak a) had the sequence LYRA<u>G</u>-$^\alpha$COSC$_6$H$_3$(3-CO$_2$H,4-NO$_2$) (SEQ ID NO 1) (observed mass 760 Da, calcd 760 Da). The N$^\alpha$(oxyethanethiol) peptide 2b (peak b) consisted of the sequence [HSCH$_2$CH$_2$O]-<u>G</u>RNTATIMMQRGNFR-$^\alpha$CONH$_2$ (SEQ ID NO 4) (observed mass 1827±1 Da, calcd 1828 Da). After one hour reaction at room temperature in the presence of added thiophenol, the ligation product, LYRA<u>GG</u>(N$^\alpha$—OCH$_2$CH$_2$SH)RNTATIMMQRGNFR-$^\alpha$CONH$_2$ (SEQ ID NO 5) (4b, observed mass 2388±1 Da, calcd 2389 Da) had formed to a significant degree, coeluting with unreacted N$^\alpha$(oxyethanethiol) peptide 2b (peak e). After further reaction overnight at room temperature, the ligation product was purified by HPLC and zinc dust was added directly to the collected peptide in HPLC eluant and stirred overnight at room temperature. Under these conditions, the zinc effectively reduced the N—O bond. Reductions of this type are possible through a variety of reagents (Keck et al. *Tetrahedron Lett.* 1995, 36, 7419–7922). The resulting peptide (peak f) gave a mass consistent with reduction of the N—O bond to produce LYRA<u>GG</u>RNTATIMMQRGNFR-$^\alpha$CONH$_2$ (SEQ ID NO 15) (5b, observed mass 2313±1 Da, calcd 2313 Da). This confirmed the rearrangement of 3b to 4b as shown in FIG. 1, since cleavage of the N—O bond in unrearranged 3b would have resulted in the formation of two distinct peptides of significantly lower masses.

EXAMPLE 3

Figure 6A:
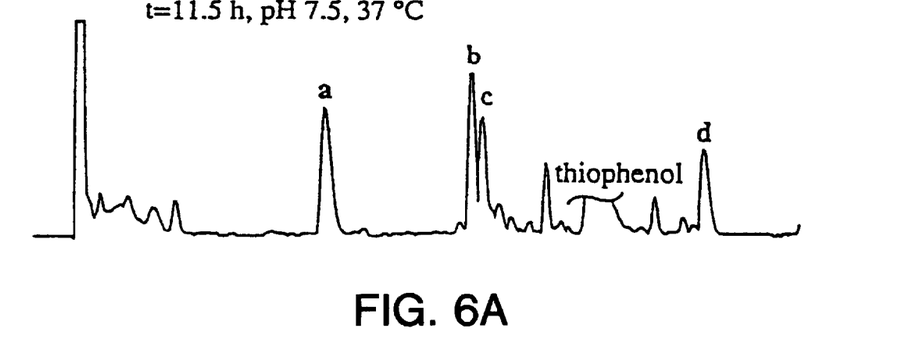
Figure 6B:
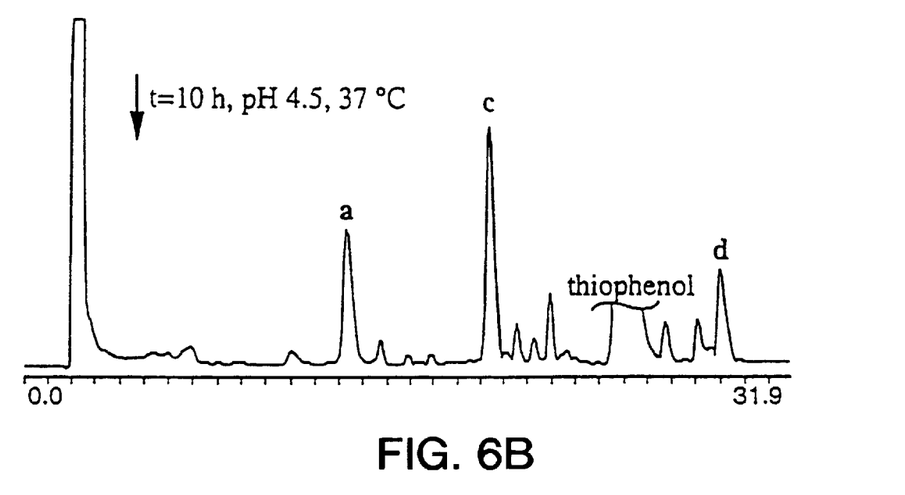
Figure 6C:
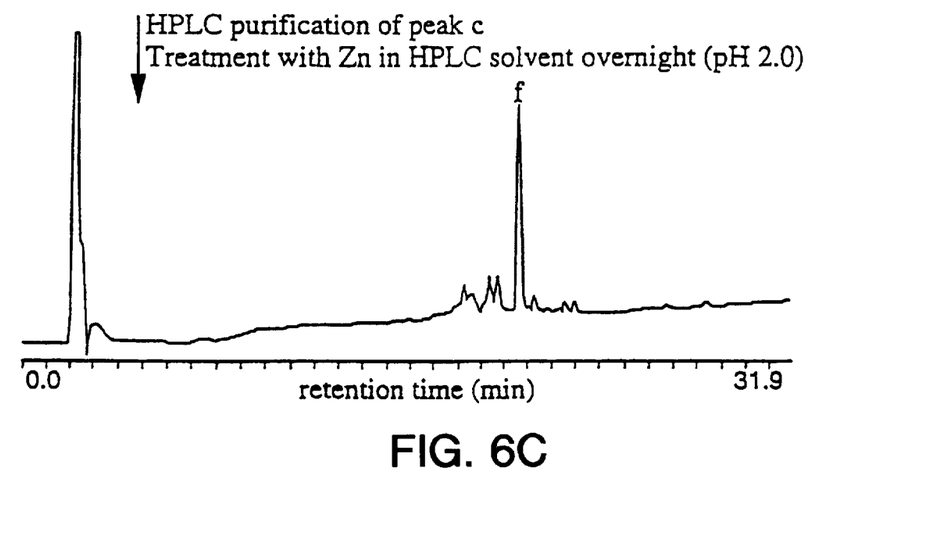

FIGS. 6A–6C show the course of example ligation #3. The peptide-$^\alpha$thioester segment 1 (peak d) consisted of a peptide with a C-terminal phenylalanine thioester [LYRA<u>F</u>-$^\alpha$COSCH$_2$C$_6$H$_5$ (SEQ ID NO 6) (observed mass 775 Da, calcd 775 Da)], thus providing a more sterically hindered model than the previous cases (example ligations #1 and #2) which involved C-terminal glycine thioesters. The N$^\alpha$(oxyethanethiol) peptide 2b (peak a) consisted of the sequence [HSCH$_2$CH$_2$O]-<u>G</u>RNTATIMMQRGNFR-$^\alpha$CONH$_2$ (SEQ ID NO 4) (observed mass 1827±1 Da, calcd 1828 Da). The presence of the more sterically hindered thioester slowed the reaction relative to the unhindered models. However, heating at 37° C. was found to accelerate the rate of initial ligation. FIG. 6A illustrates the ligation reaction after 11.5 hours at 37° C. The rate of rearrangement of 3b to 4b was slowed enough to observe the unrearranged product 3b, LYRA<u>F</u>-[$^\alpha$COSCH$_2$CH$_2$O]-<u>G</u>RNTATIMMQRGNFR-$^\alpha$CONH$_2$ (SEQ ID NO 8) (peak b, observed mass 2478±1 Da, calcd 2478 Da), eluting slightly before the rearranged product 4b, LYRA<u>FG</u>(N$^\alpha$-OCH$_2$CH$_2$SH)RNTATIMMQRGNFR-$^\alpha$CONH$_2$ (SEQ ID NO 9) (peak c, observed mass 2478±1 Da, calcd 2478 Da). Having identical masses, the unrearranged and rearranged products, 3b and 4b, were identified by their zinc reduction products. Intermediate 3b, peak b, gave two peptides upon zinc reduction with masses of 669 Da and 1753 Da corresponding to the peptide sequences LYRA<u>F</u>-$^\alpha$COOH (thioester hydrolysis) and GRNTATIMMQRGNFR-$^\alpha$CONH$_2$, respectively. It was subsequently determined that lowering the pH to 4.5 after initial ligation by diluting the crude reaction mixture (to five times the volume) with 6M guanidine.HCl, 0.1 M Na acetate, pH 4.0 accelerated the rate of rearrangement. FIG.

6B shows that rearrangement of the initial ligation product 3b to 4b (peak c) was complete after 10 hours at pH 4.5 at 37° C. HPLC purification of this peak and subsequent zinc reduction gave a peptide (peak f) of the expected mass, LYRA<u>FG</u>RNTATIMMQRGNFR-$^{\alpha}$CONH$_2$ (SEQ ID NO 18) (5b, observed mass 2403±1 Da, calcd 2404 Da).

EXAMPLE 4

LYRA<u>G</u>-$^{\alpha}$COSCH$_2$C$_6$H$_5$ 1 (SEQ ID NO 19) (observed mass 685 Da, calcd 685 Da) was ligated to [HSCH$_2$CH$_2$O]-<u>A</u>ARHTVHQRHLHG-$^{\alpha}$COOH 2b (SEQ ID NO 10) (observed mass 1595±1 Da, calcd 1596 Da) at pH 7.5. This example provided steric hindrance, in the form of an Ala residue, on the opposite side of the ligation site from example ligation #3. The rate of reaction was similiar to that of example 3, the rate being significantly slower than the unhindered examples (example ligations #1 and #2), but enhanced with heating at 37° C. Both unrearranged (3b, LYRA<u>G</u>-$^{\alpha}$[COSCH$_2$CH$_2$O]-<u>A</u>ARHTVHQRLHG-$^{\alpha}$COOH) (SEQ ID NO 11) and rearranged (4b, LYRA <u>GA</u>(N$^{\alpha}$—OCH$_2$CH$_2$SH)ARHTVHQRHLHG-$^{\alpha}$COOH) (SEQ ID NO 12) ligation products were formed, observed mass (both unrearranged and rearranged) 2156±1 Da, calcd 2157 Da. However, unlike example ligation #3, the rate of rearrangement was not enhanced by lowering the pH to 4.5 after initial ligation, though rearrangment was nearly complete after 2 days at 37° C. regardless of pH as shown by successful reduction to the amide. It should also be noted that the presence of a significant number of histidines in the final ligation product 5b (LYRA <u>GA</u>ARHTVHQRHLHG-$^{\alpha}$COOH (SEQ ID NO 20), observed mass 2080±1 Da, calcd 2080 Da) resulted in binding of the peptide to the zinc. EDTA had to be added to the HPLC buffer/Zn mixture to free the peptide from the zinc after reduction of the N—O bond. The results are summarized in FIG. 4.

EXAMPLE 5

Example 5 provides an example with steric bulk on both sides of the ligation site. LYRA<u>F</u>-$^{\alpha}$COSCH$_2$C$_6$H$_5$ 1 (SEQ ID NO 6) (observed mass 775 Da, calcd 775 Da) was ligated to [HSCH$_2$CH$_2$O]-<u>A</u>ARHTVHQRHLHG-$^{\alpha}$COOH 2b (SEQ ID NO 13) (observed mass 1595±1 Da, calcd 1596 Da) at pH 7.5. Though the initial (i.e. unrearranged) ligation product 3b was observed, LYRA<u>F</u>-$^{\alpha}$[COSCH$_2$CH$_2$O]-<u>A</u>ARHTVHQRHLHG-$^{\alpha}$COOH (SEQ ID NO 14) (observed mass 2246±1 Da, calcd 2247 Da), there was no evidence of rearrangement over time, even at lower pH. The presence of side chains on both sides of the ligation site apparently provided too much steric hindrance for the rearrangement to occur via a 6-membered ring intermediate under the conditions used. The results are summarized in FIG. 4.

The above examples emphasize the extraordinary facility of our original native ligation chemistry (Dawson et al. *Science* 1994, 266, 776–779) which recently was independently repeated in essentially identical form in model ligation studies (Tam et al. *Proc. Natl. Acad. Sci. USA* 1995, 92, 12485–12489). We have used this original native peptide bond-forming ligation reaction in the chemical synthesis of a number of proteins with full biological activity, including the chemokine IL-8 (Dawson et al. *Science* 1994, 266, 776–779), the enzymes HIV-1 protease and barnase, the serine proteinase inhibitors turkey ovomucoid third domain and eglin C, and a b/HLH transcription factor. This ligation reaction was based on principles enunciated by Max Brenner (Brenner M. Peptides. *Proceedings of the Eighth European Peptide Symposium* Beyerman, H. C., Ed., North Holland: Amsterdam, 1976; pp 1–7) and made use of chemistry first described by Wieland (Wieland et al. *Liebigs Ann. Chem.* 1953, 583, 129–149).

Experimental Protocals

General

Machine-assisted solid-phase peptide syntheses were carried out on a custom-modified Applied Biosystems 430A peptide synthesizer (Schnolzer et al. *Int. J. Pept. Protein Res.* 1992, 40, 180–193). Reverse-phase HPLC was performed on a Rainin HPLC system with 214-nm UV detection, using Vydac C-18 analytical (5 μm, 0.46×15 cm) and semipreparative (10 μm, 1.0×25 cm) columns. Chromatographic separations were achieved using linear gradients of buffer B in A (A=0.1% TFA in water, B=90% CH$_3$CN/10% water containing 0.09% TFA) over 30–60 min at 1 mL/min (analytical) or 3 L/min (semipreparative). Mass spectra of all peptide segments were obtained with a Sciex API-III electrospray quadrupole mass spectrometer; observed masses were derived from the experimental m/z values for all observed protonation states of a molecular species, using the program MacSpec (Sciex). Calculated masses were based on average isotope composition and were derived using the program MacProMass (Terry Lee and Sunil Vemuri, Beckman Research Institute, Duarte, Calif.). All other mass spectrometry was performed at The Scripps Research Institute Mass Spectrometry Facility. $^1$H NMR spectra were recorded on a Bruker 250 MHz spectrophotometer and chemical shifts are reported in parts per million downfield from Me$_4$Si. Microanalyses were performed at The Scripps Research Institute X-ray Crystallographic Facility and agreed with calculated values ±0.4%. BoC-L-amino acids and HBTU were purchased from Novabiochem (La Jolla, Calif.). 4-Hydromethylphenylacetamidomethyl (PAM) resins and diisopropylethylamine (DIEA) were obtained from Applied Biosystems (Foster City, Calif.), and methylbenzhydrylamine (MBHA) resin was obtained from Peninsula Laboratories, Inc (San Carlos, Calif.). Synthesis grade dimethylformamide (DMF) was obtained from Baker, and AR grade CH$_2$Cl$_2$ and HPLC-grade CH$_3$CN obtained from Fisher. Trifluoroacetic acid (TFA) was obtained from Halocarbon (New Jersey). HF was purchased from Matheson Gas. 4-Methylbenzyl sercaptan was obtained from Lancaster. All other reagents were AR grade or better and were obtained from Aldrich Chemical or from Fisher.

Peptide Segment Synthesis Chain Assembly

Peptides were synthesized in stepwise fashion by established machine-assisted or manual solid-phase methods using in situ neutralization/HBTU activation protocols for Boc chemistry (Schnolzer et al. *Int. J. Pept. Protein Res.* 1992, 40, 180–193). Side chain protection was as follows: BoC-Arg(p-toluenesulfonyl)-OH, BoC-Asn(xanthyl)-OH, BoC-Asp(O-cyclohexyl)-OH, BoC-His(dinitrophenyl)-OH, BoC-Thr(benzyl)-OH, and BoC-Tyr(2-bromobenzyloxycarbonyl)-OH. BoC-GlN-OH and BoC-Met-OH were used without side chain protection. Coupling reactions were monitored by quantitative ninhydrin assay (Sarin et al *Anal. Biochem.* 1981, 117, 147–157) and were typically >99%. After chain assembly was complete, peptides were deprotected and simultaneously cleaved from the resin by treatment with HF containing 5% p-cresol for 1 h at 0° C. to give the peptide-$^{\alpha}$COSH, —$^{\alpha}$CONH$_2$, or —$^{\alpha}$CO$_2$H. After removal of the HF under reduced pressure, the crude peptide was precipitated in anhydrous Et$_2$O (diethyl ether), dissolved in HPLC buffer (40–50% B) and lyophilized.

Synthesis of Peptide-$^\alpha$thioesters (1) as Shown in FIG. 1

Thioacid peptides were synthesized on the appropriate BoC-aminoacyl-S-Resins, made by coupling [4-[α-(N-t-BoC-aminoacyl-S)benzyl]phenoxy]acetic acid, DCHA salt (Canne et al. *Tetrahedron Lett.* 1995, 36, 1217–1220), (2.0 equiv) and aminomethyl-resin (1 equiv, washed with 10% DIEA in DMF; Aldrich) with HBTU (1.6 equiv; Aldrich) added as an activating agent and DIEA (1 equiv; Aldrich), in DMF (dimethylformamide). Peptide-$^\alpha$COSC$_6$H$_3$(3-CO$_2$H-4-NO$_2$) thioesters were generated by dissolving the crude peptide-$^\alpha$COSH (15–20 mgs) in 6 M guanidine.HCl, 0.1 M Na Acetate, pH 5.0–6.5, to which was added 1.5 equivalents of 5,5'-dithio-bis(2-nitrobenzoic acid) (Dawson et al. *Science* 1994, 266, 776–779). The mixture was vortexed briefly and purified after 10 min. Identity of the peptide-$^\alpha$COSC$_6$H$_3$ (3-CO$_2$H-4-NO$_2$) ester was unambigously confirmed by precise electrospray mass measurements, in contrast with Liu et al. *Tetrahedron Lett.* 1996, 37, 933–936. Peptide-$^\alpha$COSCH$_2$C$_6$H$_5$ thioesters were generated by dissolving the crude peptide-$^\alpha$COSH (15–20 mgs) in 6M guanidine.HCl, 0.1 M Na acetate, pH 4.0, to which was added 10 equivalents of benzyl bromide (Dawson et al. *Science* 1994, 266, 776–779). The mixture was vortexed briefly and purified after 1 h. LYRAG-$^\alpha$COSC$_6$H$_3$(3-C$_2$H-4-NO$_2$) (SEQ ID NO 1) (observed mass 760 Da, calcd 760 Da) was purified by semipreparative HPLC (20–60%B over 40 min) to give 20–30% yield. LYRAG-$^\alpha$COSCH$_2$C$_6$H$_5$ (SEQ ID NO 19) (observed mass 685 Da, calcd 685 Da) was purified by semipreparative HPLC ,15–45%B over 60 min) to give 25–30% yield. LYRAF-$^\alpha$COSCH$_2$C$_6$H$_5$ (SEQ ID NO 6) (observed mass 775 Da, calcd 775 Da) was purified by semipreparative HPLC (30–60%B over 60 min) to give 25–30% yield. Most of the loses in yield arose simply from HPLC recoveries.

Synthesis of N$^\alpha$(Ethanethiol) and N$^\alpha$(Oxyethanethiol) Peptides (2) as Illustrated in FIG. 2

These peptides were synthesized on either MBHA (Sigma)or the appropriate Boc-aminoacyl-OCH$_2$-PAM-resins (Sigma). After chain assembly was complete and the N$^\alpha$Boc group removed with neat TFA (two 1 min treatments) and neutralized with 10% DIEA in DMF (two 1 min treatments), the peptide was bromoacetylated by the method of Robey (Robey et al. *Anal. Biochem.* 1989, 177, 373–377). Bromoacetic acid (2.0 mmol) was dissolved in CH$_2$Cl$_2$ (2 mL) to which was added DIC (1 amol; 2-dimethylaminoisopropyl chloride hydrochloride; Aldrich or Sigma). After activation for 10–15 min to form the symmetric anhydride, the mixture was diluted with DMF (2 mL), added to the peptide-resin and coupled for 30 min. The resin was then washed with DMSO and 8a (2 M in DMSO) or 8b (1 M in DMOS) was added and allowed to react with the bromoacetylated peptide-resin for 8–23 h. The peptides were purified without further modifcation after cleavage from the resin. [(3-CO$_2$H-4-NO$_2$)—C$_6$H$_3$—S—SCH$_2$CH$_2$]-AGPAGD-$^\alpha$CONH$_2$ (SEQ ID NO 21) (2a) (observed mass 800 Da, calcd 800 Da) was purified by semipreparative HPLC (0–67%B over 60 min) to give ~24% yield. [HSCH$_2$CH$_2$O]-GRNTATIMMQRGNFR-$^\alpha$CONH$_2$(SEQ ID NO 4) (2b) (observed mass 1827±1 Da, calcd 1828 Da) was purified by semipreparative HPLC (15–40%B over 60 min) to give ~25% yield. [HSCH$_2$CH$_2$O]-AARHTVHQRHLHG-αCOOH (SEQ ID NO 10) (2b) was synthesized by the above method using the racemate of 2-bromoproprionic acid instead of bromoacetic acid. The resulting crude lyophilized product was a mixture of the desired peptide and the peptide that results from elimination of HBr from the, bromopropionylated peptide (CH$_2$=CHCO-ARHTVHQRHLHG-$^\alpha$COOH (SEQ ID NO 22), observed mass 1502±1 Da, calcd 1502 Da). The mixture was purified by semipreparative HPLC (10–40%B over 60 min) to give [HSCH$_2$CH$_2$O]-AARHTVHQRHLHG-αCOOH (SEQ ID NO 10) observed mass 1595±1 Da, calcd 1596 Da) in ~10% yield.

Synthesis of S-[(3-Carboxy-4-nitro)phenylthio]-2-aminoethanethiol (8a) as Shown in FIG. 2

2-Aminoethanethiol (1.0 g, 13.0 mmol) and 5,5'-dithio-bis(2-nitrobenzoic acid) (1.75 g, 4.4 mmol) were combined in acetonitrile (100 mL) and water (25 mL) and stirred at room temperature for 14 hr. The reaction mixture was diluted with water (450 mL) and purified by preparative reverse phase HPLC on a Waters Delta Prep 4000 with a Vydac 5.0×2.5 cm preparative C-18 column to give 8a (1.0 g, 40%) $^1$H NMR (D$_2$O): δ7.95 (d, 1H, J=8.7 Hz), 7.61 (dd, 1H, J=8.7, 2.2 Hz), 7.58 (d, 1H, J=2.2 Hz), 3.18 (t, 2H, J=6.5 Hz), 2.92 (t, 2H, J=6.7 Hz).

Synthesis of N-(2-Bromoethoxy)phthalimide (11) as Illustrated in FIG. 3

N-(2-Bromoethoxy)phthalimide (11) was synthesized by a modification of the procedure of Bauer and Sureshl (Bauer et al. *J. Org. Chem.* 1963, 28, 1604–1608). N-Hydroxyphthalimide (16.0 g, 98 mmol; Aldrich), triethylamine (30 mL, 215 mmol), and 1,2-dibromoethane (35 mL, 406 mmol; Aldrich) were combined in DMF (115 mL) and stirred at room temperature overnight. Solids were filtered and washed with DMF. The filtrate was diluted with water (800 mL) and the resulting precipitate filtered, dissolved in EtOAc (200 mL) and washed with 1 N HCl (2×50 mL), water (1×50 mL), saturated NaCl (1×50 mL) and dried over MgSO$_4$. Volatiles were removed in vacuo and the resulting solid was recrystallized from 95% EtOH to give 11 as a white solid (16.6 g, 63%). $^1$H NMR (CDCl$_3$): δ7.82 (m, 4H), 4.49 (t, 2H, J=6.9 Hz), 3.65 (t, 2H, J=6.9 Hz); FAB MS (sodium ion): calc for [C$_{10}$H$_8$BrNO$_3$, H$^+$] 291.9585, found 291.9579.

Synthesis of N-[2-[S-(4-Methylbenzyl)]mercapto]ethoxyl] phthalimide (12) as Illustrated in FIG. 3

Bromide 11 (16.6, 62 mmol), 4-methylbenzyl mercaptan (8.5 mL, 63 mmol), and DBU (9.5 mL, 64 mmol; 1,8-diazabicyclo[5.4.0]undeC-7-ene; Aldrich) were combined in benzene (150 mL) and stirred at room temperature for 8 hr. Solids were filtered, washed with benzene and the filtrate washed with 1 N HCl (2×35 mL), water (1×35 mL), saturated NaCl (1×35 mL) and dried over MgSO$_4$. Volatiles were removed in vacuo and the resulting solid recrystallized from EtOAc/hexane to yield 12 as a white solid (14.8 g, 74%) $^1$H NMR (CDCl$_3$): δ7.80 (m, 4H), 7.18 (d, 2H, J=8.0 Hz), 7.04 (d, 2H, J=8.0 Hz), 4.22 (t, 2H, J=7.4 Hz), 3.75 (s, 2H), 2.79 (t, 2H, J=7.4 Hz), 2.27 (s, 3H); FAB MS: calc for [C$_{18}$H$_{17}$NO$_3$S, H$^+$] 328.1007, found 328.1016. Anal. Calcd for C$_{18}$H$_{17}$NO$_3$S C, 66.03; H, 5.23; N, 4.28; S, 9.79. Found C, 66.04; H, 4.95; N, 4.30; S, 9.58.

Synthesis of S-(4-Methylbenzyl)-2-aminooxyethanethiol (8b) as Illustrated in FIG. 3

S-(4-methylbenzyl)-2-aminooxyethanethiol was synthesized by the method of Osby (Osby et al. *Tetrahedron Lett.* 1984, 25, 2093–2096). The N-substituted phthalimide 12 (7.4 g, 23 mmol) was suspended in isopropanol (203 mL) and water (35 mL) to which was added NaBH$_4$ (3.5 g, 92 mmol). The mixture was stirred at room temperature overnight. Acetic acid (25 mL) was slowly added till bubbling ceased, the flask stoppered and heated to 50° C. for 2–3 hr. Volatiles were removed in vacuo, the resulting solution diluted with 1 N NaOH and extracted with EtOAc (4×50 mL). The combined EtOAc extractions were washed with saturated NaCl (1×50 mL) and dried over MgSO$_4$. Volatiles were removed in vacuo and the resulting oil purified by flash chromatography (1:1 hexane:EtOAc) to yield 8b as a clear, colorless oil (3.2 g, 72%) $^1$H NMR (CDCl$_3$): δ7.21 (d, 2H, J=8.0 Hz), 7.12 (d, 2H, J=8.0 Hz), 5.40 (br s, 2H, D$_2$O ex.), 3.77 (t, 2H, J=6.5 Hz), 3.71 (s, 2H), 2.64 (t, 2H, J=6.5 Hz), 2.33 (s, 3H); FAB MS: calc for [C$_{10}$H$_{15}$NOS, H$^+$] 198.0953, found 198.0958. Anal. Calcd for C$_{10}$H$_{15}$NOS C, 60.88; H, 7.66; N, 7.10; S, 16.25. Found C, 60.79; H, 7.88; N, 7.03; S, 16.11.

---

What is claimed is:

1. A method for ligating a first oligopeptide with a second oligopeptide end-to-end to produce an oligopeptide product, the method comprising the following steps:

Step A: admixing the first and second oligopeptides in a reaction solution including a thiol that is present in a catalytic amount, the first oligopeptide including a C-terminal residue having a C-termninal thioester, the second oligopeptide including an N-terminal amino acid residue having a secondary amino group, the secondary amino group being attached to an N-linked auxiliary functional group having an unoxidized sulfhydryl moiety, the C-terminal residue being glycine when the N- terminal residue is non-glycine, the N-terminal residue being glycine when the C-terminal residue is non-glycine;

Step B: condensing the unoxidized sulfhydryl moiety of the N-linked auxiliary functional group on the first oligopeptide with the C-terminal thioester of the second oligopeptide for a time and under conditions effective to produce an intermediate oligopeptide which spontaneously rearranges to form the oligopeptide product, wherein said intermediate oligopeptide consists of the first oligopeptide and the second oligopeptide bonded together via an aminothioester bond, and said oligopeptide product consists of the first oligopeptide and the second oligopeptide bonded together via an amide bond, said amide bond bearing the N-linked auxiliary functional group; and Step C: isolating the oligopeptide product having an amide bond that bears the N-linked auxiliary functional group.

2. The method according to claim 1 wherein said thiol is selected from the group consisting of benzyl mercaptan and thiopenol.

3. The method according to claim 2 wherein the N-linked auxiliary functional group is —$(CH_2)_n$—SH, wherein $1 \leq n \leq 2$.

4. A method for ligating a first oligopeptide with a second oligopeptide end-to-end to produce an oligopeptide product, the method comprising the following steps:

Step A: admixing the first and second oligopeptides in a reaction solution including a thiol that is present in a catalytic amount, the first oligopeptide including a C-terminal residue having a C-terminal thioester, the second oligopeptide including an N-terminal amino acid residue having a secondary amino group, the secondary amino group being attached to an N-linked auxiliary functional group having an unoxidized sulfhydryl moiety, the C-terminal residue being glycine when the N- terminal residue is non-glycine, the N-terminal residue being glycine when the C-terminal residue is non-glycine;

Step B: condensing the unoxidized sulfhydryl moiety of the N-linked auxiliary functional group on the first oligopeptide with the C-terminal thioester of the second oligopeptide for a time and under conditions effective to produce an intermediate oligopeptide which spontaneously rearranges to form the oligopeptide product;

wherein said intermediate oligopeptide consists of the first oligopeptide and the second oligopeptide bonded together via an aminothioester bond, and said oligopeptide product consists of the first oligopeptide and the second oligopeptide bonded together via an amide bond, said amide bond bearing the N-linked auxiliary functional group;

Step C: reacting the oligopeptide product of step B with a reducing agent for a time and under conditions effective to remove the N-linked auxiliary functional group that is present on said amide, thereby producing a native peptide bond; and Step D: isolating the oligopeptide product having the native peptide bond.

5. A method for ligating a first oligopeptide with a second oligopeptide end-to-end to produce an oligopeptide product, the method comprising the following steps:

Step A: admixing the first and second oligopeptides in a reaction solution including a thiol that is present in a catalytic amount, the first oligopeptide including a C-terminal residue having a C-terminal thioester, the second oligopeptide including an N-terminal amino acid residue bearing an N-linked auxiliary functional group having an unoxidized sulfhydryl moiety and being respresented by —O—$(CH_2)_n$—SH, wherein $1 \leq n \leq 2$, the C-termninal residue being glycine when the N-terminal residue is non-glycine, the N-terminal residue being glycine when the C-terminal residue is non-glycine;

Step B: condensing the unoxidized sulfhydryl moiety of the N-linked auxiliary functional group on the first oligopeptide with the C-terminal thioester of the second oligopeptide for a time and under conditions effective to produce an intermediate oligopeptide which spontaneously rearranges to form the oligopeptide product;

wherein said intermediate oligopeptide consists of the first oligopeptide and the second oligopeptide bonded together via an aminothioester bond, and said oligopeptide product consists of the first oligopeptide and the second oligopeptide bonded together via an amide bond, said amide bond bearing the N-linked auxiliary functional group; and Step C: isolating the oligopeptide product having an amide bond that bears the N-linked auxiliary functional group.

6. The method according to claim 5 wherein said thiol is selected from the group consisting of benzyl mercaptan and thiopenol.

7. A method for ligating a first oligopeptide with a second oligopeptide end-to-end to produce an oligopeptide product, the method comprising the following steps:

Step A: admixing the first and second oligopeptides in a reaction solution including a thiol that is present in a catalytic amount, the first oligopeptide including a C-terminal residue having a C-terminal thioester, the second oligopeptide including an N-terminal amino acid residue bearing an N-linked auxiliary functional group having an unoxidized sulfhydryl moiety and being respresented by —O—$(CH_2)_n$—SH, wherein $1 \leq n \leq 2$, the C-terminal residue being glycine when the N-terminal residue is non-glycine, the N-terminal residue being glycine when the C-terminal residue is non-glycine;

Step B: condensing the unoxidized sulfhydryl moiety of the N-linked auxiliary functional group on the first oligopeptide with the C-terminal thioester of the second oligopeptide for a time and under conditions effective to produce an intermediate oligopeptide which spontaneously rearranges to form the oligopeptide product;

wherein said intermediate oligopeptide consists of the first oligopeptide and the second oligopeptide bonded together via an aminothioester bond, and said oligopeptide product consists of the first oligopeptide and the second oligopeptide bonded together via an amide bond, said amide bond bearing the N-linked auxiliary functional group;

Step C: reacting the oligopeptide product of step B with a reducing agent for a time and under conditions effective to remove the N-linked auxiliary functional group that is present on said amide, thereby producing a native peptide bond; and Step D: isolating the oligopeptide product having the native peptide bond.

8. The method according to claim 7 wherein the reducing agent is zinc.

* * * * *

SEQUENCE LISTING

<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<221> NAME/KEY: MOD_RES
<222> LOCATION: (4)..(5)
<223> OTHER INFORMATION: Glycine modified by C-terminal,
      alpha-((3-carboxy-4-nitrophenyl) thioester)
<223> OTHER INFORMATION: Description of Artificial Sequence: synthesized

<400> SEQUENCE: 1

Leu Tyr Arg Ala Gly
 1               5

<210> SEQ ID NO 2
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Glycine modified by
      alpha-aminoethylene-5-dithio-2nitrobenzoic acid
<223> OTHER INFORMATION: Description of Artificial Sequence:  peptide
<221> NAME/KEY: MOD_RES
<222> LOCATION: (7)
<223> OTHER INFORMATION: Aspartic acid is modified by alpha amide

<400> SEQUENCE: 2

Gly Ala Gly Pro Ala Gly Asp
 1               5

<210> SEQ ID NO 3
<211> LENGTH: 12
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-N-ethanethiol linkage
<221> NAME/KEY: MOD_RES
<222> LOCATION: (12)
<223> OTHER INFORMATION: Aspartic acid is modified by alpha amide
<223> OTHER INFORMATION: Description of Artificial Sequence:  peptide

<400> SEQUENCE: 3

Leu Tyr Arg Ala Gly Gly Ala Gly Pro Ala Gly Asp
 1               5                   10

<210> SEQ ID NO 4
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: Glycine is modified by alpha-N-oxyethanethiol
<221> NAME/KEY: MOD_RES
<222> LOCATION: (15)
<223> OTHER INFORMATION: Arginine is modified by alpha amide -continued
<223> OTHER INFORMATION: Description of Artificial Sequence: peptide

<400> SEQUENCE: 4

Gly Arg Asn Thr Ala Thr Ile Met Met Gln Arg Gly Asn Phe Arg
 1               5                  10                  15

<210> SEQ ID NO 5
<211> LENGTH: 20
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-N-oxyethanethiol linkage
<221> NAME/KEY: MOD_RES
<222> LOCATION: (20)
<223> OTHER INFORMATION: Arginine is modified by alpha amide
<223> OTHER INFORMATION: Description of Artificial Sequence: peptide

<400> SEQUENCE: 5

Leu Tyr Arg Ala Gly Gly Arg Asn Thr Ala Thr Ile Met Met Gln Arg
 1               5                  10                  15

Gly Asn Phe Arg
            20

<210> SEQ ID NO 6
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: Modified by alpha-(benzyl thioester)
<223> OTHER INFORMATION: Description of Artificial Sequence: peptide

<400> SEQUENCE: 6

Leu Tyr Arg Ala Phe
 1               5

<210> SEQ ID NO 7
<211> LENGTH: 12
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-aminoethylene-5-dithio-2-nitrobenzoic
      acid linkage
<221> NAME/KEY: MOD_RES
<222> LOCATION: (12)
<223> OTHER INFORMATION: Aspartic acid is modified by alpha amide
<223> OTHER INFORMATION: Description of Artificial Sequence: peptide

<400> SEQUENCE: 7

Leu Tyr Arg Ala Gly Gly Ala Gly Pro Ala Gly Asp
 1               5                  10

<210> SEQ ID NO 8
<211> LENGTH: 20
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-amino-oxyethylene-alpha-thioester linkage
<221> NAME/KEY: MOD_RES
<222> LOCATION: (20)
<223> OTHER INFORMATION: Arginine is modified by alpha amide
<223> OTHER INFORMATION: Description of Artificial Sequence: peptide

```
<400> SEQUENCE: 8

Leu Tyr Arg Ala Phe Gly Arg Asn Thr Ala Thr Ile Met Met Gln Arg
 1               5                  10                  15

Gly Asn Phe Arg
            20

<210> SEQ ID NO 9
<211> LENGTH: 20
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-N-oxyethanethiol linkage
<221> NAME/KEY: MOD_RES
<222> LOCATION: (20)
<223> OTHER INFORMATION: Arginine is modified by alpha amide
<223> OTHER INFORMATION: Description of Artificial Sequence: peptide

<400> SEQUENCE: 9

Leu Tyr Arg Ala Phe Gly Arg Asn Thr Ala Thr Ile Met Met Gln Arg
 1               5                  10                  15

Gly Asn Phe Arg
            20

<210> SEQ ID NO 10
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: Alanine is modified by alpha-N-oxyethanethiol
<223> OTHER INFORMATION: Description of Artificial Sequence: peptide

<400> SEQUENCE: 10

Ala Ala Arg His Thr Val His Gln Arg His Leu His Gly
 1               5                  10

<210> SEQ ID NO 11
<211> LENGTH: 18
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-amino-oxyethylene-alpha-thioester linkage
<223> OTHER INFORMATION: Description of Artificial Sequence: peptide

<400> SEQUENCE: 11

Leu Tyr Arg Ala Gly Ala Ala Arg His Thr Val His Gln Arg His Leu
 1               5                  10                  15

His Gly

<210> SEQ ID NO 12
<211> LENGTH: 18
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-N-oxyethanethiol linkage
<223> OTHER INFORMATION: Description of Artificial Sequence: peptide

<400> SEQUENCE: 12

Leu Tyr Arg Ala Gly Ala Ala Arg His Thr Val His Gln Arg His Leu
 1               5                  10                  15
```

His Gly

<210> SEQ ID NO 13
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Glycine is modified by alpha-N-ethanethiol
<221> NAME/KEY: MOD_RES
<222> LOCATION: (7)
<223> OTHER INFORMATION: Aspartic acid is modified by alpha amide
<223> OTHER INFORMATION: Description of Artificial Sequence: peptide

<400> SEQUENCE: 13

Gly Ala Gly Pro Ala Gly Asp
 1               5

<210> SEQ ID NO 14
<211> LENGTH: 18
<212> TYPE: PRT
<213> ORGANISM: Artificial Sequence
<220> FEATURE:
<221> NAME/KEY: MOD_RES
<222> LOCATION: (5)..(6)
<223> OTHER INFORMATION: Alpha-amino-oxyethylene-alpha-thioester linkage
<223> OTHER INFORMATION: Description of Artificial Sequence: peptide

<400> SEQUENCE: 14

Leu Tyr Arg Ala Phe Ala Ala Arg His Thr Val His Gln Arg His Leu
 1               5                  10                  15

His Gly

<210> SEQ ID NO 15
<211> LENGTH: 20
<212> TYPE: PRT
<213> ORGANISM: Artificial Sequence
<220> FEATURE:
<221> NAME/KEY: MOD_RES
<222> LOCATION: (20)
<223> OTHER INFORMATION: Modified by alpha amide
<221> NAME/KEY: MOD_RES
<222> LOCATION: (20)
<223> OTHER INFORMATION: Arginine is modified by alpha amide
<223> OTHER INFORMATION: Description of Artificial Sequence: peptide

<400> SEQUENCE: 15

Leu Tyr Arg Ala Gly Gly Arg Asn Thr Ala Thr Ile Met Met Gln Arg
 1               5                  10                  15

Gly Asn Phe Arg
            20

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 16

Leu Tyr Arg Ala Phe
 1               5

<210> SEQ ID NO 17
<211> LENGTH: 15
<212> TYPE: PRT

```
<213> ORGANISM: Artificial Sequence
<220> FEATURE:
<221> NAME/KEY: MOD_RES
<222> LOCATION: (15)
<223> OTHER INFORMATION: Arginine is modified by alpha amide
<223> OTHER INFORMATION: Description of Artificial Sequence: peptide

<400> SEQUENCE: 17

Gly Arg Asn Thr Ala Thr Ile Met Met Gln Arg Gly Asn Phe Arg
 1               5                  10                  15

<210> SEQ ID NO 18
<211> LENGTH: 20
<212> TYPE: PRT
<213> ORGANISM: Artificial Sequence
<220> FEATURE:
<221> NAME/KEY: MOD_RES
<222> LOCATION: (20)
<223> OTHER INFORMATION: Arginine is modified by alpha amide
<223> OTHER INFORMATION: Description of Artificial Sequence: peptide

<400> SEQUENCE: 18

Leu Tyr Arg Ala Phe Gly Arg Asn Thr Ala Thr Ile Met Met Gln Arg
 1               5                  10                  15

Gly Asn Phe Arg
            20

<210> SEQ ID NO 19
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: Glycine is modified by alpha-(benzyl thioester)
<223> OTHER INFORMATION: Description of Artificial Sequence: peptide

<400> SEQUENCE: 19

Leu Tyr Arg Ala Gly
 1               5

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: peptide

<400> SEQUENCE: 20

Leu Tyr Arg Ala Gly Ala Ala Arg His Thr Val His Gln Arg His Leu
 1               5                  10                  15

His Gly

<210> SEQ ID NO 21
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Modified by
      alpha-aminoethylene-5-dithio-2-nitrobenzoic acid
<221> NAME/KEY: MOD_RES
<222> LOCATION: (6)
<223> OTHER INFORMATION: Aspartic acid is modified by alpha amide
<223> OTHER INFORMATION: Description of Artificial Sequence: peptide

<400> SEQUENCE: 21
```

```
Ala Gly Pro Ala Gly Asp
 1               5
```

<210> SEQ ID NO 22
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: Alanine is modified by alpha-acrylamido
<223> OTHER INFORMATION: Description of Artificial Sequence: peptide

<400> SEQUENCE: 22

```
Ala Arg His Thr Val His Gln Arg His Leu His Gly
 1               5                  10
```

<210> SEQ ID NO 23
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Glycine is modified by alpha-N-ethanethiol
<223> OTHER INFORMATION: Description of Artificial Sequence: peptide

<400> SEQUENCE: 23

```
Gly Ala Gly Pro Ala Gly Asp
 1               5
```

<210> SEQ ID NO 24
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: Glycine is modified by alpha-N-oxyethanethiol
<223> OTHER INFORMATION: Description of Artificial Sequence: peptide

<400> SEQUENCE: 24

```
Gly Arg Asn Thr Ala Thr Ile Met Met Gln Arg Gly Asn Phe Arg
 1               5                  10                  15
```

<210> SEQ ID NO 25
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: Alanine is modified by alpha-N-oxyethanethiol
<223> OTHER INFORMATION: Description of Artificial Sequence: peptide

<400> SEQUENCE: 25

```
Ala Ala Arg His Thr Val His Gln Arg His Leu His Gly
 1               5                  10
```